United States Patent [19]

Swift et al.

[11] Patent Number: 4,697,622
[45] Date of Patent: Oct. 6, 1987

[54] PASSIVE FILLING DEVICE

[75] Inventors: William Swift, Fountain Valley, Calif.; Robert E. Fischell, Silver Spring, Md.

[73] Assignee: Parker Hannifin Corporation, Cleveland, Ohio

[21] Appl. No.: 874,790

[22] Filed: Jun. 13, 1986

Related U.S. Application Data

[63] Continuation of Ser. No. 616,339, Jun. 1, 1984, abandoned.

[51] Int. Cl.⁴ .................. B65B 1/04; A61B 19/00
[52] U.S. Cl. ........................ 141/1; 141/65; 141/286; 141/329; 604/407; 604/414; 604/891; 222/1; 222/85; 222/481
[58] Field of Search ............... 222/481.5, 481, 562, 222/563; 285/388, 327

[56] References Cited

U.S. PATENT DOCUMENTS

| | | | |
|---|---|---|---|
| 1,745,456 | 2/1930 | Shuler | 222/86 |
| 2,306,550 | 12/1942 | Mailey | 222/86 X |
| 2,605,938 | 8/1952 | Balcar | 222/481 X |
| 2,618,408 | 11/1952 | Taylor | 222/86 |
| 2,618,800 | 11/1952 | Raab | 222/546 X |
| 2,662,670 | 12/1953 | Voight | 222/481.5 X |
| 2,817,372 | 12/1957 | Barr, Sr. et al. | 222/85 X |
| 3,131,831 | 5/1964 | Dorchak | 222/86 |
| 3,392,883 | 7/1968 | Roberts | 222/86 |
| 3,731,681 | 5/1973 | Blackshear et al. | 604/141 |
| 3,894,538 | 7/1975 | Richter | 604/891 |
| 3,951,147 | 4/1976 | Tucker et al. | 604/189 |
| 4,063,460 | 12/1977 | Svensson | 141/65 X |
| 4,190,048 | 2/1980 | Sampson | 604/175 |
| 4,193,397 | 3/1980 | Tucker et al. | 604/56 |
| 4,221,219 | 9/1980 | Tucker | 604/141 |
| 4,229,220 | 10/1980 | Hirota | 501/46 |
| 4,299,220 | 11/1981 | Dorman | 604/118 |
| 4,360,019 | 11/1982 | Portner et al. | 604/131 |
| 4,373,527 | 2/1983 | Fischell | 128/903 |
| 4,475,914 | 10/1984 | Portnoff | 604/414 |
| 4,582,223 | 4/1986 | Kobe | 604/411 X |

FOREIGN PATENT DOCUMENTS 125944 8/1949 Sweden .................. 604/414

Primary Examiner—H. Grant Skaggs
Assistant Examiner—Gregory L. Huson
Attorney, Agent, or Firm—Christopher H. Morgan

[57] ABSTRACT

An implantable medication infusion device (10) includes a pump (34) that provides medication at below atmospheric pressure from a reservoir (32) to a catheter (12) in response to a controller (44). The infusion device (10) includes a septum fitting (14) having a septum (66) and a poppet (84) that is located in a cavity (80) that is in communication with reservoir (32). A fill needle (126) of a passive filling device opens poppet (84) and a vent needle (144) of the filling device is also opened to establish passive flow of medication from a vial (95) into the reservoir (32).

2 Claims, 5 Drawing Figures

PASSIVE FILLING DEVICE

This application is a continuation of application Ser. No. 616,339, filed June 1, 1984, and now abandoned.

BACKGROUND OF THE INVENTION

1. Field of the Invention

The subject invention relates to devices for filling implantable medication devices and, more particularly, to devices for providing a flow of liquid through the septum of a medication vial at atmospheric pressure.

2. Description of the Prior Art

The prior art includes types of implantable medication infusion devices designed to deliver medication at a selected rate. Generally, these devices have included a reservoir storing a supply of medication that would permit continued operation of the device over an extended period before the supply had to be replenished.

In many prior art infusion devices, the reservoir was refillable by access through a septum that could be penetrated by a hypodermic needle. Typically, the needle was to be pushed through the septum and the medication injected under pressure into the reservoir. When the reservoir was filled, the needle was withdrawn. Examples are shown in U.S. Pat. Nos. 3,951,147; 4,221,219; 4,229,220; and 4,360,019 as well as U.S. patent application Ser. No. 439,138 filed Nov. 11, 1981 by Robert E. Fischell.

Early infusion devices were basically pressurized reservoirs from which the medication was to be controllably gated into a catheter. Examples are shown in U.S. Pat. Nos. 4,193,397; 4,221,219; 3,731,681; 4,299,220; 3,894,538; and 3,951,147. The reservoirs of these devices were generally filled by a pressurized flow from a hypodermic needle and syringe. Other filling devices such as shown in U.S. Pat. No. 4,190,048 were also known.

One disadvantage of such pressurized reservoir devices was that, in certain failure modes, they could potentially discharge uncontrolled amounts of medication into the patient's body. Moreover, it was recognized that, in using a refill device such as a syringe that provided pressurized flow, a potential also existed that the fill needle might not be correctly placed through the septum. In that event, the medication could inadvertently be injected into the patient's body instead of the reservoir.

In later injection devices, it was recognized that a device that could maintain the medication in a reservoir having an absolute pressure slightly below atmospheric pressure would be inherently safer since the potential for discharging uncontrolled amounts of medication from the reservoir in certain failure modes did not exist. Examples of these devices are shown in U.S. Pat. Nos. 4,360,019, 4,373,527 and 4,525,165.

More recently, such below-atmospheric pressure infusion devices have incorporated an antechamber that is located between the septum and the reservoir. A poppet valve that cooperates with the septum to form the antechamber is in a normally closed position to seal off the reservoir and permit the medication therein to be maintained at below-atmospheric pressure. The poppet valve is forced open by the fill needle when it is inserted through the septum into the antechamber. This provides a flow path through the septum and into the reservoir. Thus, medication supplied through the fill needle at atmospheric pressure will flow through the antechamber and into the reservoir. Unless the fill needle is properly inserted through the septum and into the antechamber to open the poppet valve, the fill needle is not in communication with the reservoir. Under those conditions, there is no pressure differential to cause flow out of the needle. Thus, this arrangement avoids the possibility that the medication will inadvertently be injected directly into the body. An example of this type of system is shown in U.S. Pat. No. 4,573,994.

While such below-atmospheric pressure infusion devices afforded many advantages, a disadvantage was that the medication had to be actively pumped out of the reservoir. In certain devices, air that was entrained or dissolved in the fluid system could form a bubble inside the chamber of the pump. Because of the relatively high elasticity of air, there was a potential in these devices for air bubbles to compromise their efficiency as well as the accuracy of the medication dosages that they delivered.

Typically in the prior art, such below-atmospheric pressure devices were filled by use of a device that was vented to atmospheric pressure. These devices required that the medication first be removed from the commercial vial in which it was received from the manufacturer and then placed in another container such as a hypodermic syringe. The syringe or other container was then vented to atmospheric pressure. The structure of such devices typically provided cavities and chambers where air could be entrapped and ultimately carried into the infusion device. As previously explained, this could compromise the performance of the infusion device. Moreover, by requiring that the medication first be transferred from the vial to another container, these devices not only provided an additional step at which air could be introduced to the medication, but also barred any effective use of the medication directly from the vial.

Accordingly, there was a need for an improved filling device that could provide a safe flow of medication at atmospheric pressure, that did not contain pockets or cavities tending to introduce air into the fluid delivered to the reservoir and that would provide for the use of medication directly from the vial, thus allowing the use of medication that was deaerated in the vial by the pharmaceutical manufacturer.

SUMMARY OF THE INVENTION

In accordance with the subject invention, a filling device for use with an implanatable medication infusion device provides a flow of liquid medication at atmospheric pressure through the septum of a vial. The filling device includes a housing that provides an abutment surface for engagement of the vial septum and a means for maintaining the vial septum in contact with the housing. A fill needle is secured in the housing with one end of the fill needle being located longitudinally adjacent the abutment surface and the other end of the fill needle being remote from the housing. A vent needle is also secured in the housing with a first end of the vent needle being located longitudinally remote from the abutment surface and a second end of the vent needle being selectively vented to atmospheric pressure.

Preferably, the housing includes a generally cylindrical frame and retaining plug that is secured to one end of the frame. The retaining plug has an internal face that provides the abutment surface for the fill device. A maintaining means that is secured to the other end of the frame includes a cap that is suited for engagement with the bottom of the vial, and a nut that is threaded to the end of the frame. The nut cooperates with the cap to urge the cap against the bottom of the vial. In addition, a vent valve is mounted in the housing such that is can be selectively opened to communicate the second end of the vent needle to atmospheric pressure.

More preferably, the vent needle is substantially aligned with the fill needle and with the longitudinal axis of the housing. Most preferably, the fill needle is removably secured to the retaining plug by a bushing that is fastened to the fill needle and is threadingly engaged with the retaining plug.

Ohter details, objects and advantages of the subject invention will become apparent as the following description of a presently preferred embodiment thereof proceeds.

BRIEF DESCRIPTION OF THE DRAWINGS

The accompanying drawings show a presently preferred embodiment of the subject invention in which.

DESCRIPTION OF THE PREFERRED EMBODIMENT

Figure 1:
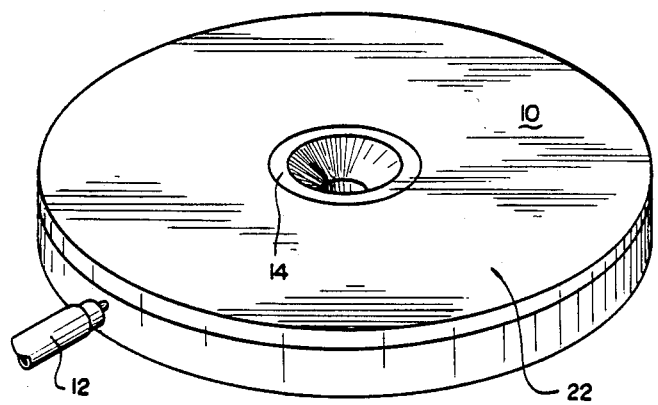
FIG. 1 is a perspective view of an implantable medication infusion device that incorporates a septum fitting and a low-pressure reservoir.
Figure 2:
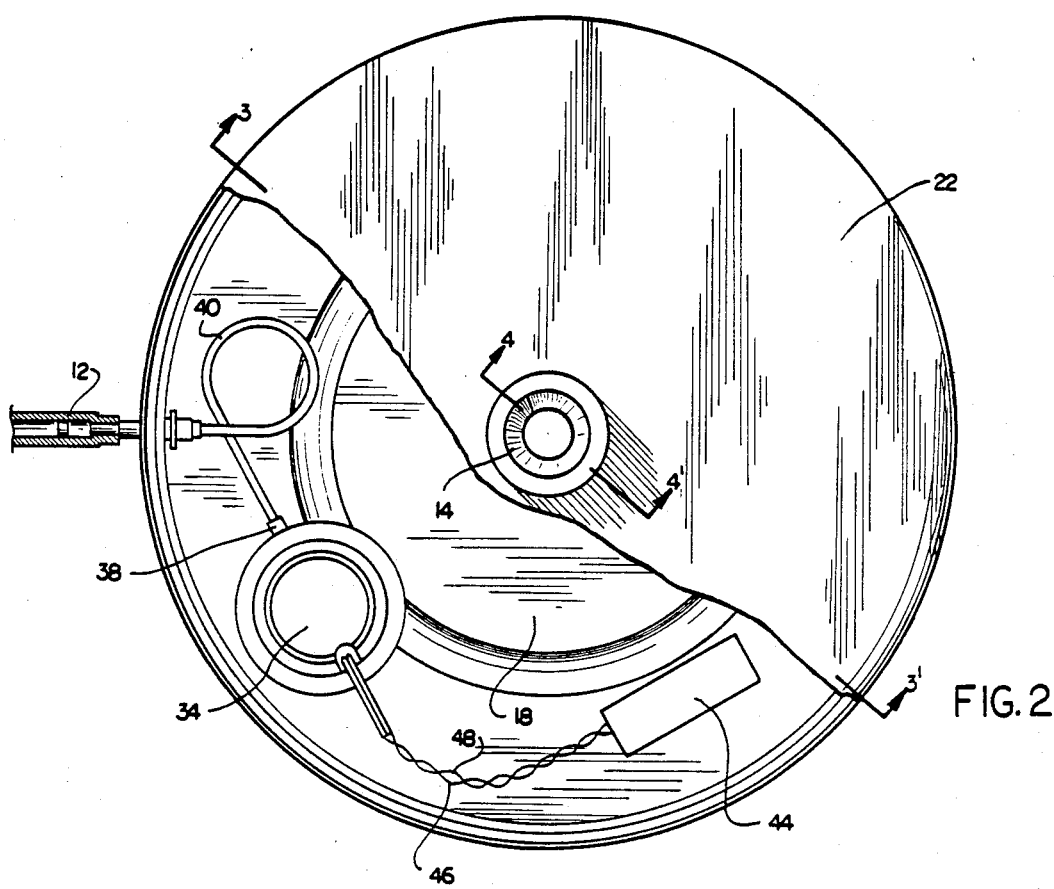
FIG. 2 is a plan view of the device shown in FIG. 1 with portions thereof broken away to better disclose the device.
Figure 3:
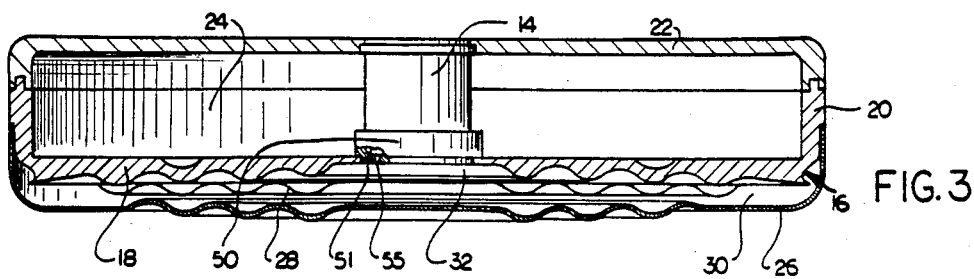
FIG. 3 is a cross-section of the device shown in FIGS. 1 and 2 taken along the lines 3–3' in FIG. 2.

FIGS. 1–3 show an implantable medication infusion device 10 that is connected to a catheter 12 and that incorporates a septum fitting 14. Infusion device 10 has a disk-shaped member 16 that includes a base 18 with a wall 20 connected to the perimeter thereof. A cover 22 is attached to one end of wall 20 and cooperates with disk-shaped member 16 to form cavity 24. A shell 26 is connected to wall 20 of member 16 and is oppositely disposed from cover 22. A diaphragm 28 is connected to base 18 inside of shell 26. Diaphragm 28 cooperates with the shell 26 and base 18 to define a pressurant chamber 30 that is filled with a gas pressurant such as Freon. Diaphragm 28 also cooperates with base 18 to define a reservoir 32.

A preferred pressurant is Freon 113 or an equivalent pressurant that will maintain a substantially constant, below one-atmosphere, saturated vapor pressure over the range of normal body temperatures. Thus, the pressurant will maintain a constant pressure in pressurant chamber 30 against diaphragm 28, so that reservoir 32 is maintained at a constant pressure that is insensitive to the volume of medication in reservoir 32. Since the saturated vapor pressure of Freon 113 is less than atmospheric pressure at seal level, the constant pressure in reservoir 32 is slightly below atmospheric pressure. Thus, in the event of a leak, medication would not be expelled under pressure from reservoir 32.

A pump 34 as shown and described in U.S. application Ser. No. 616,370 entitled "Inverted Pump" by Richard Kenyon filed concurrently herewith and hereby specifically incorporated by reference, pumps medication that is stored in reservoir 32 to catheter 12. Pump 34 has an input port (not shown) that is connected to reservoir 32 through base 18 and an output port 38 that is connected to catheter 12 through a tube 40. Pump 34 is electrically connected to electrical control circuit 44 through electrical leads 46 and 48. Control circuit 44 can be any suitable electrical control as known in the prior art for activating pump 34 at a controlled rate for a specified time period. Examples are shown and described in U.S. Pat. No. 4,373,427; U.S. patent application Ser. No. 439,139 filed Nov. 4, 1982 by Robert E. Fischell; and U.S. patent application Ser. No. 466,494 filed Feb. 15, 1983 by Robert E. Fischell; all of which are hereby incorporated by reference.

Figure 4:
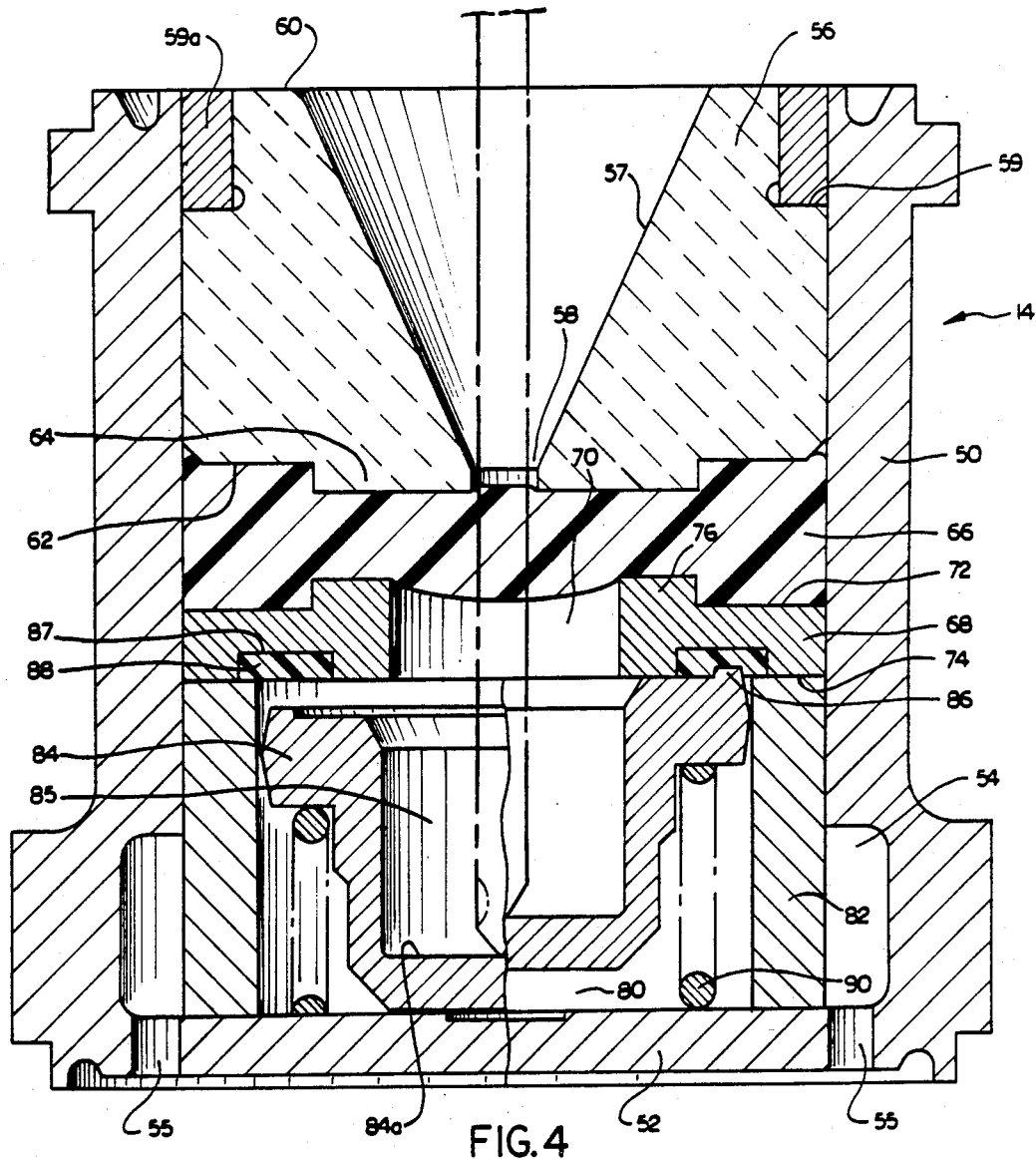
FIG. 4 is an elevation cross-section of the septum fitting incorporated in the device of FIGS. 1–3 taken along the lines 404' of FIG. 2 and having a break line to better show the action of a poppet located in the fitting.

Septum fitting 14 is connected to base 18 and cover 22 and communicates with reservoir 32 through a bore 51 in base 18. As shown in FIG. 4, septum fitting 14 includes a generally cylindrical housing 50 that is fitted in bore 51. Housing 50 has an end wall 52 at one end and is open at the opposite end. Housing 50 has an internal annular groove 54 adjacent end wall 52 and end wall 52 has a plurality of passageways or bores 55 that open to groove 54 and reservoir 32 of FIG. 3.

A fill guide 56 that has an outer face 60 and an inner face 62 is located in the open end of housing 50. Fill guide 56 includes an external shoulder 59. A retainer ring 59a is connected adjacent the open end of housing 56 and cooperates with shoulder 59 to retain fill guide 56 in the open end of housing 50. Fill guide 56 also includes a central extension 64 that is located on inner face 62 as well a conically shaped interior surface 57 and a cylindrical passageway 58. Conical surface 57 is longitudinally aligned in a perpendicular direction between outer face 60 and inner face 62 with the base of conical surface 57 intersecting outer face 60. Cylindrical passageway 58 is located at the apical end of conical surface 57 with one end of passageway 58 intersecting conical surface 57 and the other end of passageway 58 intersecting the end face of extension 64. Thus, conical surface 57 and passageway 58 cooperate to provide a passageway through fill guide 56. Preferably, fill guide 56 is made of ceramic material.

A septum 66 is located inside housing 50 adjacent inner face 62 of fill guide 56. Septum 66 contacts inner face 62 and extension 64 of fill guide 56. An annular band 68 is located inside housing 50 adjacent the surface of septum 66 that is oppositely disposed from the surface that engages fill guide. Annular band 68 has a first end face 72 and a second end face 74. An aperture 70 extends between first and second end faces 72 and 74 and is generally aligned with passageway 58 of fill guide 56. Annular band 68 also includes a central ring 76 that is connected to first end face 72 and circumscribes aperture 70. Septum 66 contacts central ring 76 and first end face 72 of annular band 68.

Annular band 68 cooperates with housing 50 and septum 66 to define a cavity 80 wherein an annular filter 82 is located. Annular filter 82 filters medication as it is delivered to the reservoir as hereafter explained and also longitudinally locates annular band 68 with respect to end wall 52. A poppet 84 includes a lip portion 86 cooperates with septum 66 and annular band 68 to define an antechamber 85. Poppet 84 is concentrically located inside filter 82 and is movable between second end face 74 of annular band 68 (as shown on the right side of the break line in FIG. 4) and end wall 52 (as shown on the left side of break line of FIG. 4). Annular band 68 further includes an annular groove 87 located in second end face 74 and a seating ring 88 is fitted within said annular groove 87. A biasing means such as spring 90 is provided to urge the lip 86 of poppet 84 toward seating ring 88. Thus, in its normally biased position, a seal is formed between seating ring 88 and lip 86 of poppet 84.

In the operation of the implantable infusion device shown in FIGS. 1-4, liquid medication is stored in reservoir 32 at a pressure slightly below atmospheric pressure as determined by the pressure of the gas pressurant in chamber 30 against diaphragm 28.

FIG. 2 shows that control circuit 44 causes pump 34 to draw medication from reservoir 32 and expel it at a controlled rate through output port 38, tube 40 and into catheter 12. As known in the art, control circuit 44 in cooperation with pump 34 can be designed and constructed to provide mediation to catheter 12 in accordance with various rate profiles as desired.

When reservoir 32 is to be refilled, a noncoring needle (shown in phantom) is injected into septum fitting 14. The needle passes through the space defined by conical surface 57 and is guided to passageway 58 at the central portion of the fitting by conical surface 57. The needle passes through passageway 58, penetrates septum 66, enters antechamber 85 and contacts the bottom surface 84a of poppet 84. The needle is then advanced further causing poppet 84 to be moved into contact with end wall 52 of housing 50.

The movement of poppet 84 in response to the needle draws lip 86 away from seating ring 88 and breaks the seal therebetween. Thus, antechamber 85 is placed in communication with reservoir 32 through annular filter 82, annular groove 54, and bore 55. Medication in the needle at atmospheric pressure is caused to flow into antechamber 85 and then reservoir 32 because of the pressure differential in reservoir 32 which is maintained at below-atmospheric pressure by the pressurant in chamber 30.

When a given volume of medication has been allowed to flow, the needle is withdrawn from antechamber 85 and septum fitting 14. As the needle is withdrawn, poppet 84 follows the movement of the needle until lip 86 engages seating ring 88 to form seal therebetween.

Figure 5:
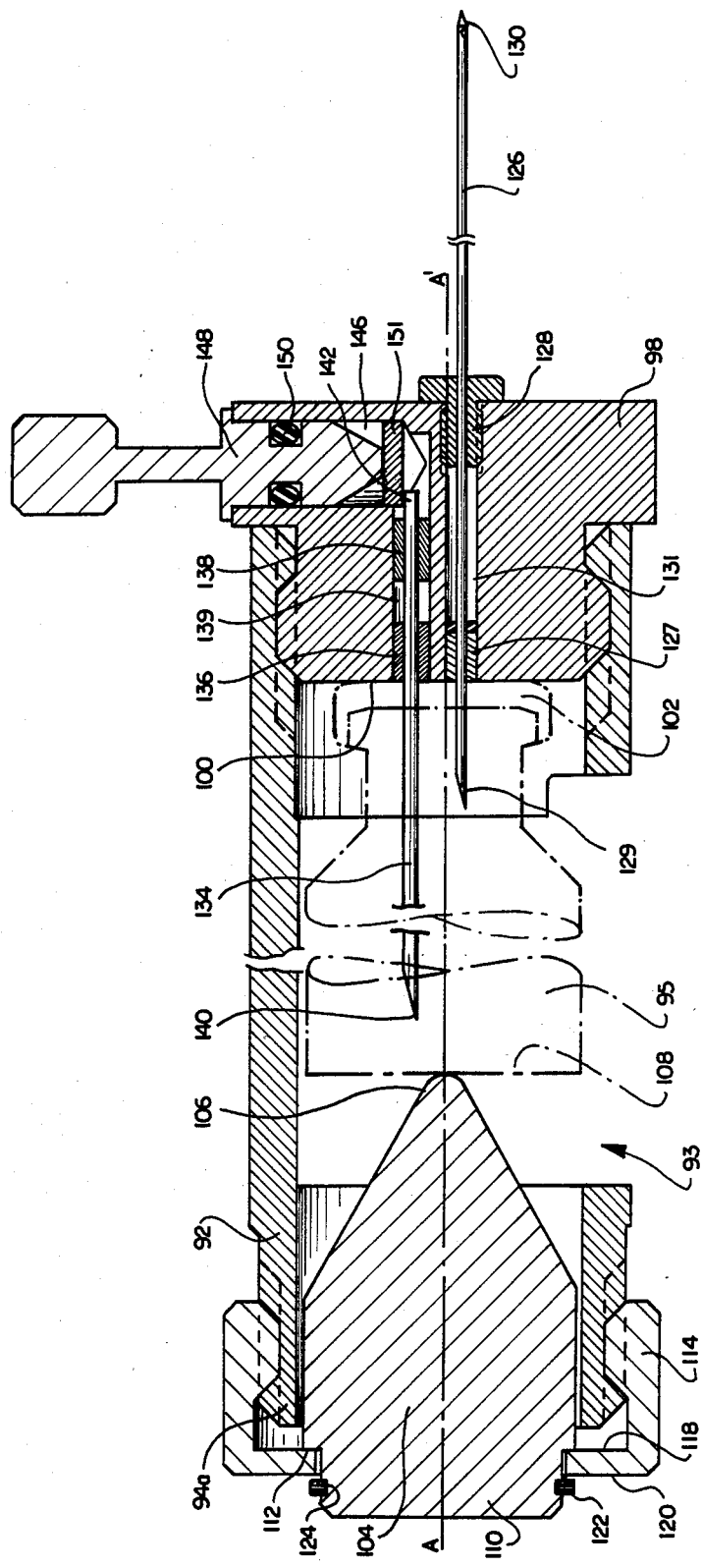
FIG. 5 shows an elevational cross-section of a filling device in accordance with the subject invention and adapted for use with the infusion device of FIGS. 1–4.

FIG. 5 shows a medication fill device in accordance with the subject invention that will provide no chambers or enlargements in the fill needle that tend to trap air that could be drawn into the infusion device as reservoir 32 is refilled. In the specific embodiment of FIG. 5, a housing includes a generally cylindrical frame 92 having a longitudinal central axis A-A'. Frame 92 is of sufficient diameter that a commercially available medication vial 95 of standard size can be inserted and removed through an open end 94a. In the example of the preferred embodiment, medication vial 95, contains substantially deaerated medication. Frame 92 also includes an opening 93 that is of sufficient size to serve as a window to view the level of medication in vial 95.

A retaining plug 98 is threadingly secured to the end of frame 92 that is opposite from end 94a. Retaining plug 98 has an internal face 100 that provides an abutment surface for the engagement of a septum 102 on vial 95 as is hereafter more fully explained.

A means for maintaining vial septum 102 in contact with internal face 100 of retaining plug 98, is connected to end 94a of frame 92 after vial 95 has been inserted therethrough. In the preferred embodiment of FIG. 5, the maintaining means includes a cap 104 having an internal end 106 for engagement with the bottom surface 108 of vial 95. Preferably, cap 104 is of resilient, compressible material and internal end 106 is generally in the shape of a cone with the apex oriented to abut bottom surface 108. Cap 104 also includes an external end 110 that is oppositely disposed from internal end 106 and a shoulder 112 that is longitudinally adjacent external end 110.

The means for maintaining the septum also includes a nut 114 having an internal face 118 and an oppositely disposed external face 120. Nut 114 is threadingly connected to end 94a of frame 92. Internal face 118 cooperates with shoulder 112 of cap 104 to urge cap 104 against bottom 108 of vial 95.

The means for maintaining the vial against internal face 100 further includes a retaining ring 122 that is fitted in an annular cavity 124 located adjacent external end 110 of cap 104. Retaining ring 122 radially extends from cap 104 adjacent external face 120 of nut 114 and cooperates with the shoulder of cap 104 to longitudinally maintain nut 124 therebetween.

A fill needle 126 is secured in retaining plug 98 by bushings 127 and 128 such that it is longitudinally aligned with axis A-A' of frame 92 and orthogonally projects from internal face 100. Fill needle 126 has an input end 129 and an output end 130. Input end 129 of fill needle 126 is located longitudinally adjacent internal face 100. Output end 130 is located longitudinally remote from the side of retaining plug 98 that is oppositely disposed from internal face 100 by a length sufficient to operate poppet 84 (FIG. 4) of an infusion device that is implanted in a patient.

Fill needle 126 is a unitary member that has no couplings, junctions, cavities or joints between input end 129 and output end 130. In contrast, fill needle 126 has an internal passage of substantially constant cross-sectional area and shape between ends 129 and 130. Accordingly, there are no chambers or pockets therein in which air can be trapped.

Bushings 127 and 128 secure fill needle 125 in retaining plug 98 such that is is removable from the plug. Specifically, bushings 127 and 128 are permanently fastened to fill needle 126 by brazing, welding, or other permanent means. Bushing 127 is slidably maintained in a bore 131 of retaining plug 98. Bushing 128 is threadingly engaged in the end of bore 131 such that fill needle 126 can be removed by unthreading bushing 128.

A vent needle 134 is also secured in retaining plug 98 by bushings 136 and 138 that are permanently fastened inside a bore 139 such that it is longitudinally aligned with fill needle 126 and projects from internal face 100. Vent needle 134 has an insertion end 140 and a vent end 142. Insertion end 140 is located longitudinally remote from internal face 100 by a length slightly less than the height of vial 94 such that when vial septum 102 contacts internal face 100, insertion end 140 of vent needle 134 is located longitudinally adjacent the interior surface of bottom 108 of vial 95.

Vent end 142 of vent needle 134 is in communication with a vent valve formed by a cavity 146 in cooperation with a valve plug 148. Cavity 146 is located in retaining plug 98 and opened to end 142 of vent needle 134. Valve plug 148 is slidingly engaged in cavity 146 and includes a dynamic seal such as an o-ring 150 that is concentrically located on valve plug 148 and slidingly engages the wall of cavity 146. Valve plug 148 is selectively removed from cavity 146 to communicate vent end 142 of vent needle 134 to atmospheric pressure.

Preferably, a bacterial filter 151 is mounted in cavity 146 between valve plug 148 and vent needle 134 to block bacteria from entering vial 95 through vent needle 134 when plug 148 is removed. Typically, filter 151 is of substantially 0.2 micron pore size.

In the operation of the fill device of FIG. 5, with vent valve 144 closed, and cap 104 and nut 114 removed from the end of frame 92, vial 95 is longitudinally inserted into frame 92 through the open end 94a. Vial 95 is then advanced through frame 92 until fill needle 126 and vent needle 134 penetrate vial septum 102 and septum 102 abuts internal face 100. Due to the location of input end 129 of the fill needle 126 and insertion end 140 of vent needle 134 with respect to internal face 100, insertion end 140 is longitudinally adjacent the interior bottom surface 108 of vial 95 and input end 129 is longitudinally adjacent the interior surface of vial septum 102. Cap 104 is then placed over the end of frame 94 and nut 114 is rotated such that is cooperates with shoulder 112 to engage bottom 108 with end 106 to urge vial 95 firmly against internal face 100.

The conical shape of cap 104 provides a limited contact area between end 106 and bottom 108 and thus limits the torsional forces applied to vial 95 and septum 102. Thus, the conical shape of cap 104 limits the torsional stress on vial septum 102 that tends to cause leakage of the seal formed between septum and needles 126 and 134.

As previously explained, end 130 of fill needle 126 is inserted into cavity 80 of septum valve 12 to open poppet 84 and establish fluid communication between end 130 and reservoir 32 which is maintained at below-atmospheric pressure. With vial 95 secured in contact with internal face 100, vent valve 144 is opened to communicate vent end 142 of vent needle 134 to atmospheric pressure. Thus, a pressure differential exists between end 142 of vent needle 134 and end 130 of fill needle 126. This pressure differential establishes a flow of air from end 142 to end 140 of vent needle 134 and a flow of medication from input end 129 to output end 130 of fill needle 126 and through cavity 80 to reservoir 32. The longitudinal dimension between the end 140 of vent needle 132 and the end 129 of fill needle 126 is designed with regard to the cross-section area of vial 95 and the volume capacity such that the volume of vial 95 exceeds the volume of reservoir 32 when medication flow will automatically stop.

If end 130 of fill needle 126 is not properly inserted in antechamber 85 to open poppet 84, end 130 of fill needle 126 will not be exposed to below-atmospheric pressure and no flow will be provided.

Since poppet 84 is opened by contact with end 130 of fill needle 128, end 130 may tend to become dull with usage. Further use of a dulled needle 128 will cause excessive wear and coring of septum 66 of septum fitting 12 resulting in premature exhaustion of device 10. However, in accordance with the subject invention, fill needle 128 is replaceable so that end 130 can be kept sharp and accelerated wear of septum 66 avoided.

The medication fill device herein described accommodates a commercially available vial and can fill a pump reservoir directly therefrom. Thus, in using the disclosed fill device, it is unnecessary to remove the medication from the vial and place it in a hypodermic syringe or other intermediate container. Thus, the disclosed fill device is particularly advantageous in applications where the use of deaerated medication is of consequence. Because the disclosed device removes the medication directly from the vial, the medication can be deaerated by the pharmaceutical manufacturer at the time that the vial is filled. For such applications, the disclosed fill device avoids a separate deaeration step for the user of the medication.

While a presently preferred embodiment of the subject invention has been shown and described, the invention is not limited thereto, but can be otherwise variously embodied within the scope of the following claims.

We claim:

1. A method for filling a medication infusion apparatus comprising the steps of:

inserting a commercial style medication vial containing deaerated medication into a housing containing a hollow needle and a hollow vent needle, causing one end of said fill needle and said vent needle to be inserted through a septum closing one end of said vial and causing said fill needle and vent needle to be in fluid communication with said deaerated medication;

inserting the other end of said fill needle through a self-sealing system located on said medication infusion apparatus and into a fluid chamber maintained at a pressure lower than atmospheric pressure; and allowing air at atmospheric pressure to enter into said vial through said vent needle, until the appropriate amount of the deaerated medication has been drawn into said fluid chamber from said vial.

2. The method of claim 1 further comprising the step of:

filtering air entry into said vent needle with a biological filter thereby blocking entry of bacteria into said vial.

* * * * *

UNITED STATES PATENT AND TRADEMARK OFFICE
CERTIFICATE OF CORRECTION

PATENT NO. : 4,697,622

DATED : October 6, 1987

INVENTOR(S) : William Swift and Robert E. Fischell

It is certified that error appears in the above—identified patent and that said Letters Patent is hereby corrected as shown below:

In Claim 1, Column 8, Line 35, change "hollow needle" to "hollow fill needle".

Signed and Sealed this

Twelfth Day of June, 1990

Attest:

HARRY F. MANBECK, JR.

Attesting Officer

Commissioner of Patents and Trademarks